(12) United States Patent
Frances et al.

(10) Patent No.: US 6,743,883 B1
(45) Date of Patent: Jun. 1, 2004

(54) INITIATOR FOR POLYMERIZING AND/OR CROSS-LINKING POLYORGANOSILOXANES WITH CROSS-LINKABLE FUNCTIONAL GROUPS, CORRESPONDING COMPOSITIONS AND THEIR USES

(75) Inventors: Jean-Marc Frances, Meyzieu (FR); Thomas Deforth, Lyons (FR)

(73) Assignee: Rhodia Chimie, Boulogne Billancourt Cedex (FR)

( * ) Notice: Subject to any disclaimer, the term of this patent is extended or adjusted under 35 U.S.C. 154(b) by 0 days.

(21) Appl. No.: 10/111,517

(22) PCT Filed: Oct. 6, 2000

(86) PCT No.: PCT/FR00/02789
§ 371 (c)(1),
(2), (4) Date: Apr. 25, 2002

(87) PCT Pub. No.: WO01/30903
PCT Pub. Date: May 3, 2001

(30) Foreign Application Priority Data

Oct. 29, 1999 (FR) ............................................ 99 13620

(51) Int. Cl.$^7$ ................................................ C08G 77/08
(52) U.S. Cl. ............................ 528/13; 528/43; 528/32; 568/1; 502/202; 106/35; 526/279; 549/215
(58) Field of Search .............................. 528/13, 43, 32; 568/1; 502/202; 106/35; 526/279; 549/215

(56) References Cited

U.S. PATENT DOCUMENTS 4,412,039 A * 10/1983 Alberts et al.
4,772,325 A     9/1988 Kwan et al.
5,973,020 A    10/1999 Kerr, III et al.

\* cited by examiner

*Primary Examiner*—Kuo-Liang Peng
(74) *Attorney, Agent, or Firm*—Burns, Doane, Swecker & Mathis, L.L.P.

(57) ABSTRACT

The invention relates to a heat-activated initiator for polymerising and/or cross-linking polyorganosiloxane-type monomers, oligomers and/or polymers with organofunctional groups, comprising a boron derivative of formula (I): $(A)_xB(R')_y$, wherein the symbols R' are the same or different and represent an alkyl or alkenyl radical in $C_1$–$C_{12}$, an alkoxy radical in $C_1$–$C_{12}$, a phenyl radical substituted by at least one electroattractor element, an aryl radical containing at least two aromatic rings such as biphenyl, naphthyl, optionally substituted by at least one electroattractor element, especially a halogen atom (particularly fluorine), or an electroattractor group, especially a $CF_3$, $NO_2$, CN group; and a radical —$C_2H_4$—$Si(Q)_3$ with the symbols Q being the same or different and representing an alkyl or alkoxy group in $C_1$ to $C_{10}$ or a siloxane oligomer with less than 10 silicon atoms. The invention also relates to a corresponding cross-linkable composition and to the uses thereof.

19 Claims, No Drawings

INITIATOR FOR POLYMERIZING AND/OR CROSS-LINKING POLYORGANOSILOXANES WITH CROSS-LINKABLE FUNCTIONAL GROUPS, CORRESPONDING COMPOSITIONS AND THEIR USES

The present invention relates to the field of initiation of reactions for polymerising and/or cross-linking polyorganosiloxane-type monomers, oligomers and/or polymers containing reactive functional radicals capable of forming intra- and inter-catenary bridges so as to obtain a corresponding matrix.

More particularly, its main aim is to provide new initiators which will lead to these matrices.

This type of matrix is of particular interest for the preparation of multiple compositions such as dental materials, adhesives, sealants, jointing products and adhesive finishes.

The applications targeted more particularly by the invention are the use of compositions for the preparation of dental compositions such as dental prostheses or dental restoration materials and of compositions of the non-adhesive coating type used, in particular, to produce coatings on objects such as solid articles or substrates, in particular paper substrate, fabric, polyester or polyolefin type polymer film, aluminium substrate and/or metal substrate such as tin plate.

More precisely, the present invention relates to new initiators containing at least one boron derivative for the initiation and progress of resin or polymer forming reactions, starting from substrate derived from polyorganosiloxane-type monomers, oligomers and/or polymers with reactive organofunctional groups.

The reactions more particularly concerned are those in which agents act as direct promoters of the inter- and/or intra-catonary bonds In the present case, these reactions are initiated by heat activation.

In the present description, the resins and polymers obtained are prepared from polyorganosiloxane-type monomers, oligomers and/or polymers and contain, in their structure, organofunctional groups, for example of the epoxide, oxetane, dioxolane and/or alkenylether type, which react after activation of the initiators according to the invention described hereinafter. In addition organic monomers, oligomers and/or polymers which may be added to the polymerisation medium containing the aforementioned species may also be used.

The present invention also relates to compositions containing the basic materials such as cross-linkable polyorganosiloxane-type monomers, oligomers and/or polymers, the initiators described hereinafter and optionally one or more additives selected from those generally known in the applications for which these compositions are intended.

The initiators generally used to initiate the formation of resins or polymers on the basis of the aforementioned polymerisation and/or cross-linking of organosiloxane substrates may be divided into three categories, depending on their mode of activation. This mode of activation may in fact be thermal, photochemical or by an electron beam.

Conventionally, the initiator used, which is generally a cationic photoinitiator, releases a strong acid under irradiation during photochemical cross-linking such as UV radiation This strong acid catalyses the cationic polymerisation reaction of the functional groups. Initiators of this type are described, in particular, in EP-0 562 897. The initiating salts in that patent represent significant technical progress over the formerly known initiators of the onium salt or organometallic complex type, and in particular over those of which the anion of the initiating salt is $SbF_6$— which is one of the only ones which has the correct performance but which poses serious problems infuse owing to the presence of heavy metals.

Thermal cross-linking, for its part, necessitates very high temperatures generally higher than 150° C. to trigger cross-linking. This second type of initiator is used, in particular, to cross-link silicones such as those described hereinafter (S1 to S15) in a thin layer and for epoxide or oxetanes.

One of the main aims of the present invention is specifically to propose new heat-activated initiators for triggering the cross-linking of polyorganosiloxane-type monomers, oligomers and/or polymers with functional groups at a temperature lower than 150° C. and preferably lower than 100° C., or even substantially at ambient temperature.

More particularly, the present invention relates firstly to a heat-activated initiator for polymerising and/or cross-linking monomers, oligomers and/or polymers with organofunctional groups, comprising a boron derivative of formula (I)

wherein the symbols R' are the same or different and represent
  a linear or branched $C_1$–$C_{12}$, preferably $C_1$–$C_8$ alkyl or alkenyl radical, optionally substituted by at least one electron-withdrawing element, in particular a halogen atom (more particularly fluorine) or an electron-withdrawing group, for example the $CF_3$, $NO_2$, CN groups,
  a linear or branched $C_1$–$C_{12}$, preferably $C_1$–$C_8$ alkoxy radical, optionally substituted by at least one electron-withdrawing element, in particular a halogen atom (more particularly fluorine) or an electron-withdrawing group, for example the $CF_3$, $NO_2$, CN groups,
  a phenyl radical substituted by at least one electron-withdrawing element, in particular a halogen atom (more particularly fluorine) or an electron-withdrawing group, for example the $CF_3$, $NO_2$, CN groups,
  an aryl radical containing at least two aromatic rings such as biphenyl, naphthyl, optionally substituted by at least one electron-withdrawing element, in particular a halogen atom (more particularly fluorine) or an electron-withdrawing group, for example the $CF_3$, $NO_2$, CN groups,
  a —$C_2H_4$—Si(Q)$_3$ radical with the symbols Q being the same or different as representing a $C_1$ to $C_{10}$ alkyl or alkoxy group or a siloxane oligomer with less than 10 silicone atoms, substituted, if necessary, by a radical of formula B(R')$_2$ with R' as defined above or
  two R' groups may be bound to one another so as to form, with the boron atom to which they are bound, a cycle containing 5 or 10 atoms wherein said cycle may be saturated, unsaturated, bridged or aromatic and may comprise one or more heteroatoms selected from oxygen, nitrogen and boron atoms, wherein the boron atom present in said cycle may itself be substituted by a radical as defined for A or R' in general formula I, the symbols A are independent of one another and represent:
a hydrogen atom
a halogen atom or
a hydroxyl radical,
x represents 0 or the integer 1 or 2 and y represents an integer 1, 2 or 3 wherein the sum of x+y is equal to 3 and its solvated forms.

The initiators according to the invention are generally very hygroscopic compounds. Consequently, these compounds may be found in the form of a mixture between the compound as defined in general formula I and its various hydrated form(s). Similarly, when this initiator is formulated with a solvent, the formation of solvated derivatives is observed. This phenomenon can be observed with aprotic solvents such as ethers, esters and silicones or protic solvents such as alcohols, carboxylic acids, silanols, amines, thiols, water or mixtures thereof.

Consequently, the present invention also extends to these solvated forms.

The new initiators are of particular interest in terms of reactivity insofar as they are active at low concentrations and advantageously necessitate only small amounts of energy to carry out cross-linking. In fact, they may be activated at a temperature lower than 150° C., preferably lower than 100° C., or even at ambient temperature.

The initiators according to the invention may also be associated with a conventional initiator such as a cationic photoinitiator. This is particularly advantageous in terms of profitability insofar as it is thus possible significantly to reduce the effective quantity of conventional initiator. Furthermore, cross-linking and/or polymerisation are totally completed.

It has accordingly been found that the claimed initiators are particularly advantageous in terms of profitability and cost for industrial processes.

More preferably, the symbols R' of general formula (I) are selected so as to give the boron atom to which they are bound adequate steric hindrance to give it adequate protection from oxidation and/or hydration phenomena. In this instance, the initiators of general formula (I) in which at least one of the symbols R' and preferably at least two of them represent a phenyl or aryl radical are of particular interest.

Similarly, it is advantageous that the symbols R' are substituted and, in particular, by electron-withdrawing elements and/or groups so as to give the boron atom electronegativity which is compatible with its electrophilic properties. Initiators of general formula I which the symbols R', together with the symbols A contribute to a $\sigma_p$ at least equal to that of 3 ($C_6H_4F$) radicals have accordingly been found to be particularly effective.

Particularly preferred according to the invention are initiators corresponding to general formula (Ia)

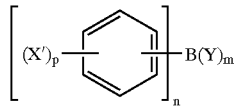

(Ia)

in which
n represents an integer between 1 and 3 and m an integer between 0 and 2 wherein the sum of n and m is equal to 3,
the symbols Y are the same or different and represent
a) a hydrogen atom,
b) a hydroxyl group,
c) a halogen atom,
d) a linear or branched $C_1$–$C_{12}$, preferably $C_1$–$C_8$ alkyl or alkenyl radical, preferably substituted by at least one electron-withdrawing element such as a halogen atom and in particular a fluorine atom,
e) a linear or branched $C_1$ to $C_{12}$, preferably $C_1$ to $C_8$ alkoxy radical, preferably substituted by at least one electron-withdrawing element such as a halogen atom and in particular a fluorine atom,
f) a —$C_2H_4$—$Si(Q)_3$ wherein Q represents a $C_1$ to $C_{10}$ alkyl or alkoxy group or a siloxane oligomer with less than 10 silicone atoms, if necessary substituted by a radical of formula $B(R')_2$ wherein R' is as defined above, or
g) two groups Y may be bound so as to form, with the boron atom to which they are bound, a $C_5$ to $C_{10}$ cycle wherein said cycle may be saturated, unsaturated, bridged and/or aromatic and may comprise one or more heteroatoms selected from the oxygen, nitrogen and boron atoms, wherein the boron atom present in said cycle can itself be substituted by a radical as defined for Y in general formula (Ia) and the symbols X' are the same or different and represent
a halogen atom, preferably a fluorine atom,
a linear, branched, mono- or polycyclic, saturated, unsaturated or aromatic $C_1$ to $C_{12}$, preferably $C_1$ to $C_8$, hydrocarbon radical preferably substituted by at least one electron-withdrawing element such as a halogen atom and in particular a fluorine atom or a linear or branched, mono-, poly or perhalogenated $C_1$ to $C_{12}$, preferably $C_1$ to $C_8$, alkyl radical, in particular with fluorine as halogen atom, and
the indices p are the same or different and represent an integer between 0 and 5, preferably with at least one of the symbols p being greater than 3 and more preferably equal to 5.

The initiators of general formula (Ia) in which Y corresponds to definitions a), b), c), d) and e) are of particular interest.

The following compounds, in particular, may be mentioned as examples of the claimed initiators:

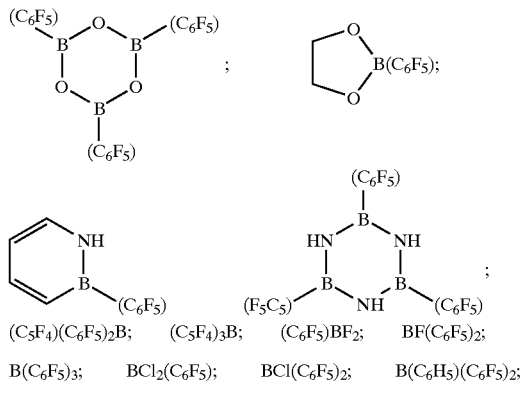

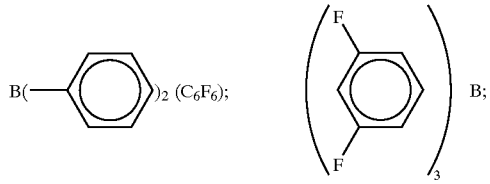

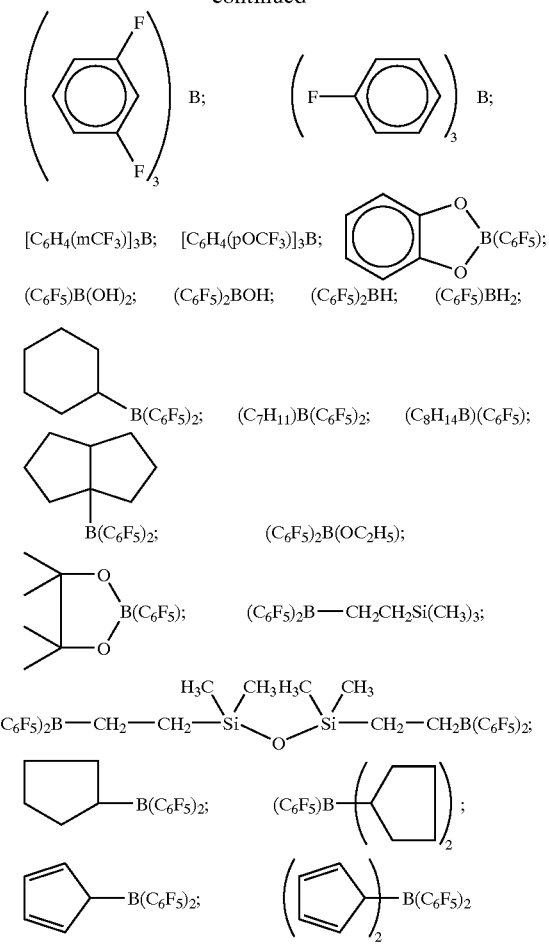

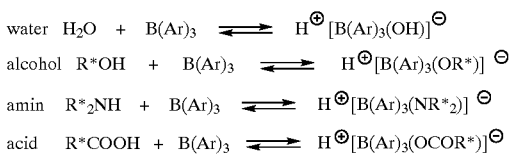

The initiators according to the invention may be used in the form in which they emerge from their preparation process, for example in solid or liquid form or in solution in at least one appropriate solvent, in monomer, oligomer and/or polymer compositions which are intended to be polymerised and/or cross-linked. In the scope of the invention, the term solvent covers products which make solid initiators soluble and products which dilute liquid or solid initiators.

Preferably, the initiators are generally used in solution in a solvent. The proportions by weight of initiating agent(s) on the one hand and the solvent on the other hand are between 0.1 and 99 parts per 100 parts of solvent and preferably 10 to 50 parts.

This initiator solution is therefore used to prepare a bath with the cross-linkable monomers, oligomers and/or polymers with functional groups such that the concentration of the initiator or initiators present is between 0.01 and 5% by weight in said bath and preferably between 0.05 and 0.5%.

The solvents which may be used for the initiators are very numerous and varied and are selected according to the initiator used and the other components of the composition of the invention. Generally, the solvents may be alcohols, esters, ethers, ketones, traces of water and carbonates.

The alcohols commonly used are paratolylethanol, isopropylbenzyl alcohol, benzyl alcohol, methanol, ethanol, propanol, isopropanol and butanol. The ethers commonly used are methoxy-2-ethanol, ethoxy-2-ethanol, diethyleneglycol. The conventional esters are dibutylmaleate, dimethylethylmalonate, methyl salycilate, dioctyl adipate, butyl tartrate, ethyl lactate, n-butyl lactate, isopropyl lactate. Other solvents which may be used for the initiator bath and falling in the other categories of solvents mentioned hereinbefore are acetonitrile, benzonitrile, acetone, cyclohexanone and tetrahydrofuran.

Furthermore, from among the solvents which may be used to dissolve the initiators), certain types of proton donor organic solvents and certain types of hydroxylated carboxylic acid esters also have the property of significantly improving their performance in terms of reactivity and kinetics.

As mentioned hereinbefore, in solution, the initiator claimed according to the invention can tend toward a solvated form. The various forms can coexist within the solvent under the influence of an equilibrium. Examples of these salvation phenomena include, in particular water $H_2O + B(Ar)_3 \rightleftharpoons H^{\oplus}[B(Ar)_3(OH)]^{\ominus}$ alcohol $R^*OH + B(Ar)_3 \rightleftharpoons H^{\oplus}[B(Ar)_3(OR^*)]^{\ominus}$ amin $R^*_2NH + B(Ar)_3 \rightleftharpoons H^{\oplus}[B(Ar)_3(NR^*_2)]^{\ominus}$ acid $R^*COOH + B(Ar)_3 \rightleftharpoons H^{\oplus}[B(Ar)_3(OCOR^*)]^{\ominus}$ The present invention also extends to the solvated forms of the claimed initiators.

According to another of its aspects, the present invention relates secondly to polymerisable and/or cross-linkable compositions containing at least one polymerisable and/or cross-linkable polyorganosiloxane-type monomer, oligomer and/or polymer carrying functional groups, an effective quantity of at least one initiator of the type corresponding to the invention and described hereinbefore, optionally a polymerisation and/or cross-linking accelerator and optionally again one or more additives selected from among those generally known in the applications for which these compositions are intended.

Effective quantity of initiator according to the invention means an adequate quantity to initiate polymerisation and/or cross-linking. This quantity is generally between 0.0001 and 5 parts by weight, usually between 0.001 and 0.5 parts by weight in order to polymerise and/or cross-link 100 parts by weight of the dry substance in polyorganosiloxane monomers, oligomers and/or polymers with organofunctional groups.

As mentioned hereinbefore, the claimed initiator may be present in the polymerisable and/or cross-linkable composition in association with a conventional initiator such as, in particular, a cationic photoinitiator. Suitable conventional photoinitiators include, in particular, those described in the patent EP 562 897. They may also be corresponding iodonium or sulphonium salts of hexafluorophosphate or hexafluoro-antimonate.

In this type of association, the two types of initiator are used in a proportion of 0.01 to 5 parts by weight in the case of the photoinitiator and $1 \times 10^{-5}$ to 5 parts by weight in the case of the claimed initiator, preferably $1 \times 10^{-4}$ to $1 \times 10^{-2}$ in the case of the initiator claimed for polymerisation and/or cross-linking per 100 parts by weight of polyorganosiloxane-type polymerisable and/or cross-linkable monomer(s), oligomer(s) and/or polymer(s) carrying functional groups.

Photocross-linkable coatings are thus obtained cationically, which develop few interactions with adhesives and in particular with acrylic adhesives.

The claimed polymerisable and/or cross-linkable composition is preferably based on polyorganosiloxane-type monomer(s) and/or oligomer(s) and/or polymer(s) consisting of units of formula (II) and terminated by units of formula (III) or cyclic groups consisting of units of formula (II) shown hereinafter:

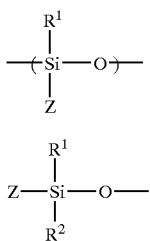  (II)

$$-\!\!\left(\!\!\begin{array}{c}R^1\\|\\Si-O\\|\\Z\end{array}\!\!\right)\!\!-$$

(III)

$$Z-\!\!\begin{array}{c}R^1\\|\\Si-O-\\|\\R^2\end{array}$$

in which
the symbols $R^1$ and $R^2$ are similar or different and represent:
- a linear or branched alkyl radical containing 1 to 8 carbon atoms, optionally substituted by at least one halogen, preferably fluorine, the alkyl radicals preferably being methyl, ethyl, propyl, octyl and 3,3,3-trifluoropropyl,
- a cycloalkyl radical containing between 5 and 8 cyclic carbon atoms, optionally substituted,
- an aryl radical containing between 6 and 12 carbon atoms which may be substituted, preferably phenyl or dichlorophenyl,
- an aralkyl portion having an alkyl portion containing between 5 and 14 carbon atoms and an aryl portion containing between 6 and 12 carbon atoms, optionally substituted on the aryl portion by halogens, alkyls and/or alkoxyls containing 1 to 3 carbon atoms, the symbols Z are similar or different and represent:
- an $R^1$ and/or $R^2$ group,
- a hydrogen radical,
- and/or a cross-linkable organofunctional group, preferably an epoxy-functional, oxetane-functional, dioxolane-functional and/or alkenylether-functional group, bound to the silicone of the polyorganosiloxane via a divalent radical containing 2 to 20 carbon atoms and possibly containing at least one heteroatom, preferably oxygen,
- wherein at least one of the symbols Z represents a cross-linkable functional organic group.

According to an advantageous variant of the invention, the polyorganosiloxanes used contain 1 to 10 organofunctional groups per macromolecular chain. For an epoxy functional group, this corresponds to epoxide contents varying from 20 to 2,000 molar meq/100 g of polyorganosiloxane.

The linear polyorganosiloxanes may be oils having dynamic viscosity at 25° C. of approx. 10 to 10,000 mPa.s at 25° C., generally of approx. 20 to 5,000 mPa.s at 25° C. and even more preferably of 20 to 600 mPa.s at 25° C. or gums having a molecular mass of approx. 1,000,000.

If cyclic polyorganosiloxanes are used, they consist of units (II) which may be, for example, of the dialkylsiloxy or alkylarylsiloxy type. These cyclic polyorganosiloxanes have a viscosity of approx. 1 to 5,000 mPa.s.

Examples of divalent radicals binding an organofunctional group of the epoxy and/or oxetane type include those of the following formulae:

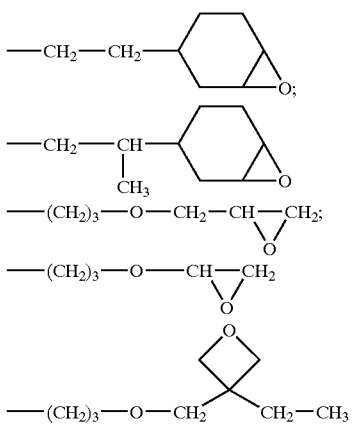

Examples of organofunctional groups of the alkenyl ether type include those contained in the following formulae:

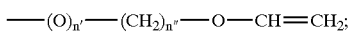

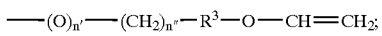

in which.
n' represents 0 or 1 and n" represents an integer between 1 and 5
$R^3$ represents
a linear, branched or cyclic $C_1$ to $C_{12}$, optionally substituted, alkylene radical, or
a $C_5$ to C12 arylene radical, preferably phenylene, optionally substituted, preferably by one to three $C_1$ to $C_6$ alkyl groups,
$R^4$ represents a linear or branched $C_1$ to $C_6$ alkyl radical.
Examples of dioxolane groups include those contained in the following formulae:

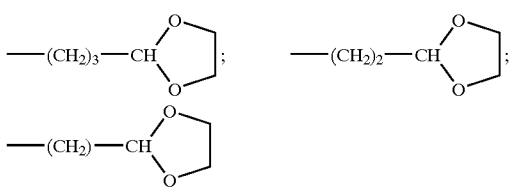

The epoxy or alkenylether-functional polyorganosiloxanes are generally in the form of fluids having a viscosity at 25° C. of 10 to 10,000 mm²/s and preferably 20 to 600 mm²/s.

The dynamic viscosity at 25° C. of all the silicones considered in the present description may be measured using a BROOKFIELD viscosimeter corresponding to AFNOR standard NFT 76 102 of February 1972.

This type of compound is described, in particular, in the patents DE-A-4.009.889; EP-A-396.130; EP-A-355.381; EP-A-105.341; FR-A-2.110.115; FR-A-2.526.800.

The alkenylether-functional polyorganosiloxanes may be prepared by hydrosilylation reaction between the oils containing Si—H units and vinyloxy-functional compounds such as allylvinylether, allylvinyloxyethoxybenzene; etc.

Epoxy-functional polyorganosiloxanes may be prepared by hydrosilylation reaction between oils containing Si—H units and epoxy-functional compounds such as vinyl-4 cyclohexeneoxide, allylglycidylether, etc.

The oxetane-functional polyorganosiloxanes may be prepared by hydrosilylation of unsaturated oxetanes or condensation of oxetanes containing a hydroxy-function.

The dioxolane-functional polyorganosiloxanes may be prepared by hydrosilylation of unsaturated dioxolanes.

Polyorganosiloxanes of which the units of formulae (II) and/or (III) comprise at least one phenyl, tolyl or dichlorophenyl radical as radical $R^1$ are quite particularly suitable for the invention.

The silicones best suited for the subject of the invention are described hereinafter and comprise at least one epoxide, alkenylether or oxetane group.

In the following formulae, X may represent an alkyl, cyclohexyl; trifluoropropyl; perfluoroalkyl; alkoxy or hydroxypropyl group, R a $C_1$ to $C_{10}$ alkyl, $C_1$ to $C_{10}$ cyclohexyl, trifluoropropyl or perfluoroalkyl radical and ($0 \leq a \leq 1000$); ($1 \leq b \leq 1000$).

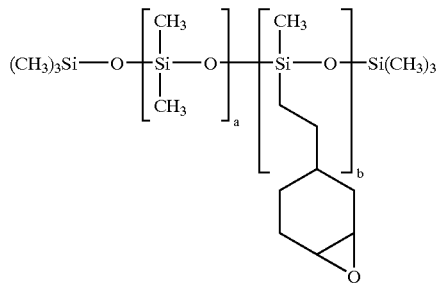

S1

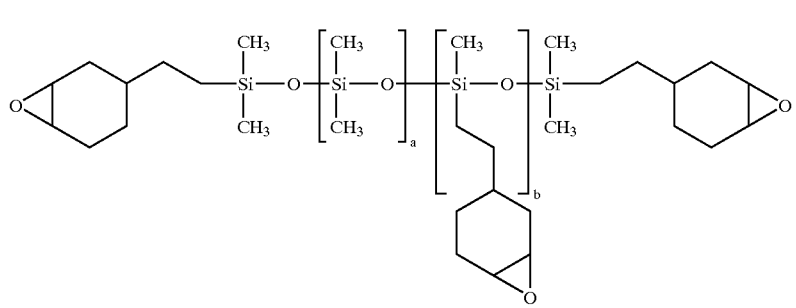

S2

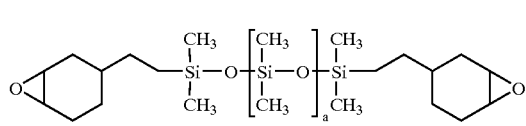

S3

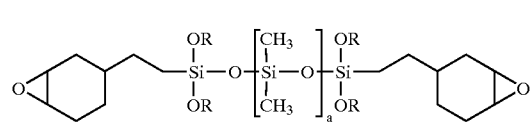

S4

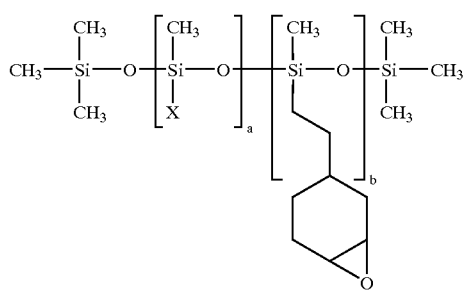

S5

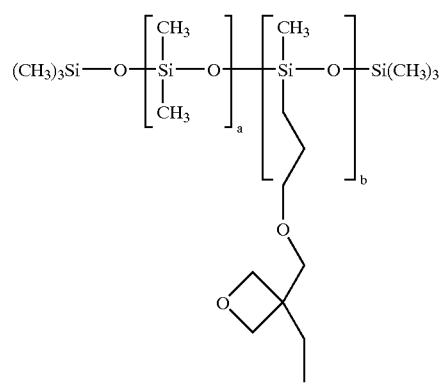

S6

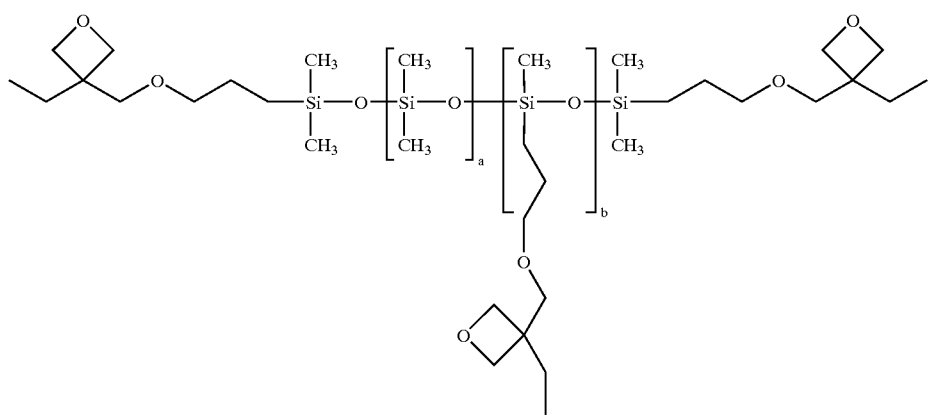
S7
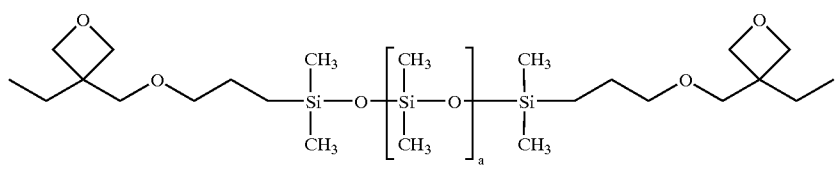
S8
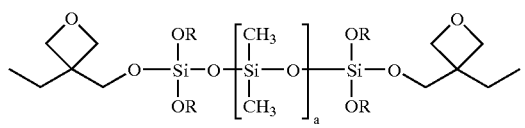
S9
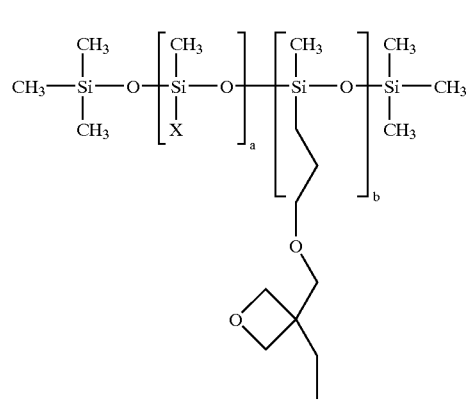
S10
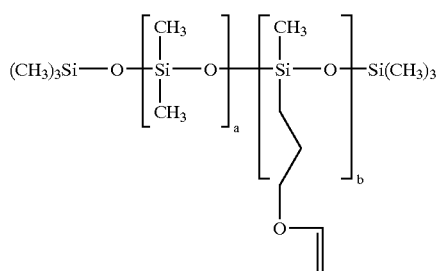
S11
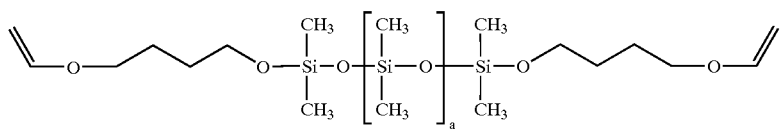
S12
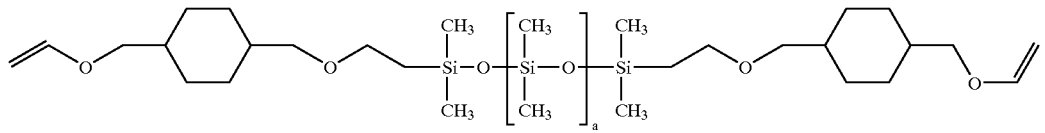
S13

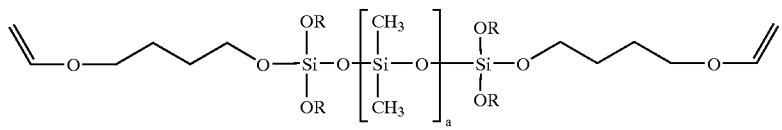

S14

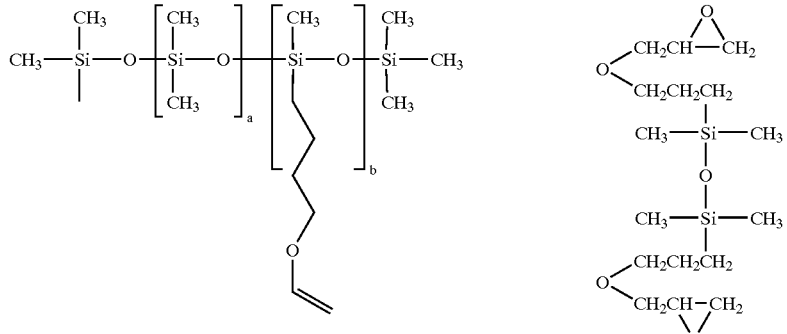

S15

S16

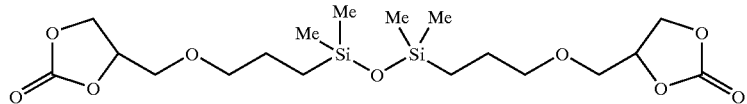

S17

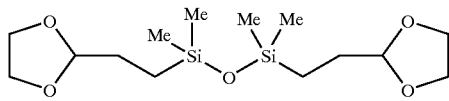

S18

According to an interesting disposition of the second subject of the invention, the polymerisable and/or cross-linkable composition is based on *polyorganosiloxane-type monomer(s) and/or oligomer(s) and/or polymer(s) such as those defined hereinbefore and on organic-type, in particular hydrocarbon-containing monomer(s), oligomer(s) or polymer(s).

In this instance, the following organic monomers, oligomers or polymers in which n can vary from 0 to 1,000 are particularly suitable for the invention.

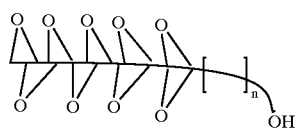

KRATON™EKP 207

(01)

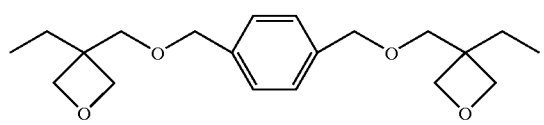

(02)

(03)

(04)

(05)

-continued (06)

(07)

According to a third interesting disposition of the second subject of the invention, the polymerisable and/or cross-linkable composition is based on polyorganosiloxane-type and optionally organic-type monomer(s) and/or oligomer(s) and/or polymer(s) in particular hydrocarbon-containing monomer(s) and/or oligomer(s) and/or polymer(s).

To use the initiators according to the invention, various sources of heat may be used to carry out polymerisation and/or cross-linking of the monomers, oligomers and/or polymers. In the particular case where the initiator according to the invention is used with a cationic photoinitiator, the heat inherent in the irradiation used to activate said photoinitiator may be sufficient simultaneously to activate the claimed initiator.

Conventionally, the compositions according to the invention can also comprise inter alia one or more additives selected as a function of the intended final application.

The additives may be, in particular, compounds possibly in the form of polymers containing mobile hydrogens such as alcohols, glycols and polyols which are useful for improving the flexibility of the material which has hardened after polymerisation and/or cross-linking; these include, for example, polycaprolactone polyols, in particular the polymer initially obtained from 2-ethyl-2-(hydroxymethyl)-1,3-propane-diol and 2-oxepanone such as the product TONE POLYOL-301 sold by UNION CARBIDE or the other industrial polymers TONE POLYOL 201 and TONE POLYOL 12703 from UNION CARBIDE. Further suitable additives include long chain alkyl diacids, the fatty esters of epoxidised or non-epoxidised unsaturated acids, for example epoxidised soya oil or epoxidised linseed oil, epoxidised 2-ethylhexyl ester, 2-ethylhexyl epoxy stearate, octyl epoxy stearate, epoxidised acrylic esters, epoxidised acrylates of soya oil, acrylates of epoxidised linseed oil, glycolpolypropylene diglycidyl ether, long chain aliphatic epoxides, etc.

This additive may be, in particular, a stabilisation additive. It is generally an aminated agent containing at least one amine of which the boiling point is higher than 150° C. and preferably higher than 200° C. This amine may be a secondary amine or a tertiary amine.

In particular, the amines described in WO 98/07798 may be used.

It should be noted that the majority of hindered amines used as stabilisers to light ("HALS" type) have been found to be very good candidates for meeting the requirements of the stabilisers used in the scope of the invention even though their intrinsic property of stability to light is not directly related to the mode of action of the stabilising aminated agents of the compositions according to the invention. In this regard, it is possible to use the various types of hindered amines in the documents EP 162 524 and EP 263 561.

Numerous types of commercially available hindered amines have given good results, in particular:

- the TINUVIN products sold by CIBA GEIGY, in particular the products TINUVIN 144 and TINUVIN 765 described hereinafter,
- the CYAGARD products sold by CYTEC, in particular the product CYAGARD UV 1164L, and
- the SANDUVAR products, in particular the product SANDUVAR 3055, described hereinafter and sold by SANDOZ.

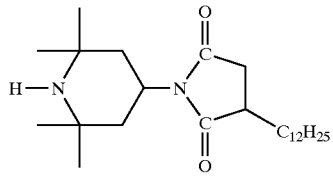

Tinuvin 144

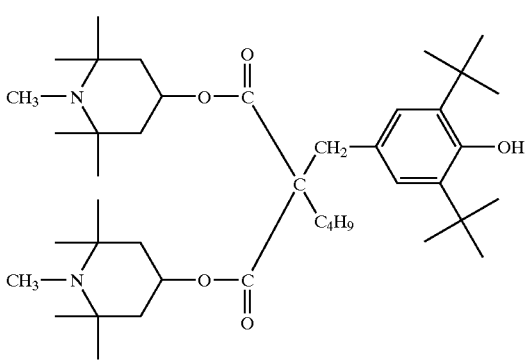

Tinuvin 765

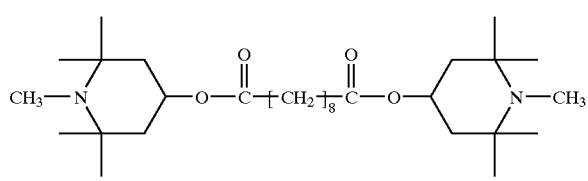

Sanduvar 3055

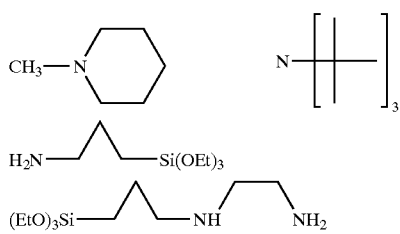

Other types of amines corresponding to the following formulae are also good candidates for use in the compositions of the invention; by way of example, the structure of some of these amines is given hereinafter:

The percentage of aminated agent generally used by weight relative to the total weight of the silicone matrix is between 1 and 1,000 ppm and preferably between 10 and 100 ppm. In the case of HALS type aminated agent, the quantity is approx. 20 to 100 ppm.

The compositions according to the invention may also contain other ingredients such as adhesion modulators for increasing or reducing the forces of adhesion obtained from the polyorganosiloxane alone (silicone linear resins or polymers carrying vinyl, epoxy, vinyl ether, alcohol functions), pigments, photosensitisers, fungicidal, bactericidal and anti-microbial agents, corrosion inhibitors, etc.

Whatever the nature of the polymerisable matrix, these may also be, for example: fillers such as, in particular, synthetic fibres, titanium dioxide, silica from precipitation or combustion; soluble dyes; oxidation and corrosion inhibitors; organosilicon or other adhesion modulators; fungicidal, bactericidal, anti-microbial agents; and/or any other material which does not interfere with the activity of the initiator.

The present invention also relates to resins or polymers obtainable from the above-described compositions.

In the particular case where the compositions are used to prepare dental compositions, various types of fillers may be used. The fillers are selected as a function of the final use of the dental composition: they affect significant properties such as, the appearance, the penetration of UV radiation and the mechanical and physical properties of the material obtained after cross-linking and/or polymerisation of the dental composition.

Suitable reinforcing fillers include treated or untreated pyrogenated silica fillers, amorphous silica fillers, quartz, glass or non-vitreous fillers based on zirconium, barium, calcium, fluorine, aluminium, titanium, zinc oxides, borosilicates, aluminosilicates, talcum, spherosil, ytterbium trifluoride, polymer-based fillers in the form of crushed powder such as inert or functionalised polymethylmethacrylates, polyepoxides or polycarbonates. Examples include:

LUXASELF inert fillers based on polymethylmethacrylate from the company UGL which contain pink pigment and may be used in the dental field, hexamethyldisilazane-treated fumed silica fillers having a specific surface area of 200 m²/g, untreated fumed silica charges ("aerosil" AE200 sold by DEGUSSA).

The fillers, and in particular the silica fillers, may be treated prior to use at 120° C. with a quantity smaller than 10% p/p of silicone comprising at least one unit of formula

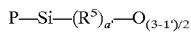
$$P-Si-(R^5)_{a'}-O_{(3-1')/2}$$

wherein P, which may be the same or different, is an organic substituent containing at least one reactive epoxy and/or alkenyl ether and/or oxetane and/or dioxolane and/or carbonate function, $R^5$, which may be the same or different, is a $C_1$ to $C_6$ alkyl, cycloalkyl, aryl, vinyl, hydrogen, alkoxy, preferably lower alkyl radical, a'=0, 1, 2 or 3, with at least one silicon atom.

The polymer described hereinafter wherein P=epoxide and P=trialkoxysilyl may be mentioned as an example

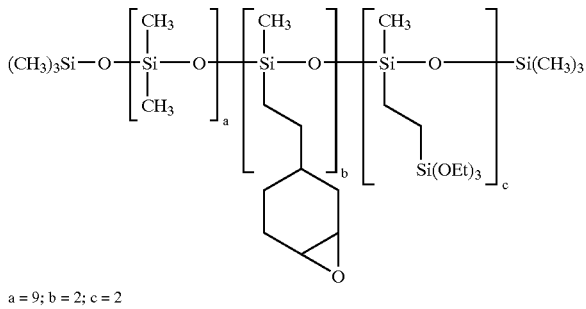

a = 9; b = 2; c = 2

The dental compositions according to the invention may be used for numerous dental applications and in particular in the field of dental prostheses, in the field of dental restoration and in the field of temporary teeth.

Advantageously, in dental use, the compositions according to the invention allow rapid setting at ambient temperature and a significant reduction in the phenomenon of shrinkage normally observed with conventional silicone compositions.

In the field of dental prostheses, the dental composition according to the invention is preferably in the form of a single product containing the various components ("monocomponent") and this facilitates the use thereof. If necessary, this product may be stabilised by organic derivatives containing amine functions in accordance with the teaching of the document WO 98/07798.

The product may be deposited by means of a syringe directly onto the plaster model or in a mould. It is then polymerised (polymerisation by possible successive layers) by means of a UV lamp (visible light spectrum 200 to 500 nm). An aesthetic dental prosthesis is generally produced in 10 to 15 minutes.

It should be noted that the products obtained from the dental composition according to the invention are not porous. Thus, after polishing with a felt brush, for example, if necessary, the surfaces of the dental prostheses obtained is smooth and shiny and therefore does not necessitate the use of varnish. Applications in the field of dental prostheses are essentially those of complete denture.

In the field of dental restoration, the dental composition according to the invention may be used as material for filling front and back teeth in different colours (for example "VITA"), which is quick and easy to use.

As the dental composition is non-toxic and may be polymerised in thick layers, it is not essential to polymerise the material in successive layers. Generally, a single injection of the dental composition will suffice.

The preparations for dental prostheses and for restoration materials are carried out by conventional methods in the art.

With regard to the other applications, the compositions according to the invention may be used as they are or in solution in an organic solvent. They are useful in the field of non-adhesive coatings on cellulose containing materials, paints, the encapsulation of electric and electronic components, coatings for textiles and for the cladding of optical fibres.

They are of particular interest when used as such to make a material non-adhesive, such as metal sheets, glass, plastics material or paper to other materials to which they normally adhere. The composition advantageously has a viscosity not exceeding 5,000 mPa.s, preferably not exceeding 4,000 mpa.s at 25° C.

The invention therefore also relates to a process for making articles (for example sheets) non-adhesive to surfaces to which they normally adhere, the process being characterised in that it involves applying a quantity of composition of the invention generally of between 0.1 and 5 g per m² of surface to be coated and cross-linking or polymerising the composition by exposing it to a source of heat.

This invention also extends to coatings derived from the claimed resin and/or polymer compositions. The coating may be of the varnish, adhesive, non-adhesive type and/or an ink. Silicone coatings may also be obtained in the field of encapsulation of electronic components or claddings for optical fibres.

The solvent-free, in other words undiluted, compositions are applied using devices capable of depositing small quantities of liquids uniformly. The device known as "sliding Helio" comprising, in particular, two superimposed cylinders may be used for this purpose: the role of the lowest cylinder immersed in the coating tank containing the composition is to impregnate the highest cylinder in a very thin layer, the role of the highest cylinder therefore being to deposit the desired quantities of composition with which it is impregnated on the paper, this dosage being obtained by adjusting the respective speed of the two cylinders which rotate in opposite directions to one another.

The quantities of compositions deposited on the substrates vary and usually range between 0.1 and 5 g/m² of treated surface. These quantities depend on the nature of the substrates and the desired non-adhesive properties. They are usually between 0.5 and 1.5 g/m² in the case of non-porous substrates.

The present invention also relates to the use of a compound of general formula I as defined hereinbefore as a heat-activated polymerisation and/or cross-linking initiator for polyorganosiloxane-type monomers, oligomers and/or polymers with organofunctional groups, in particular as defined hereinbefore.

The present invention also relates to the articles (for example sheets) consisting of a solid material (metal, glass, plastics material, paper, etc.) of which at least one surface is coated with the above-mentioned thermally-cross-linked composition.

The following examples are given as an illustration and cannot be considered as a limit to the scope and essence of the invention.

EXAMPLE 1

The polymer (S1)

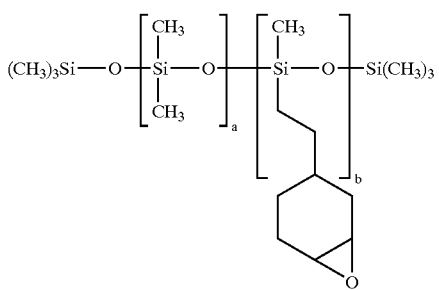

is used in a proportion of 10 g such that a=80; b=7.

This polymer is or is not stabilised by 50 ppm of a hindered amine used as light stabiliser, namely TINUVIN 765®.

The initiator $(C_6F_5)_3$ B designated P1, 18% in solution in dibutylether, is added.

The concentration of the trispentafluorophenylborane is 0.18% in silicone.

The setting time of the silicone polymer after mixing with stirring is recorded. The gel time corresponding to passage from the liquid state to the solid state is less than 30 seconds at 25° C. and found to be 10 s.

EXAMPLE 2

The same experiment as in example 1 is carried out while adding the initiator P1 in a proportion of 9% in butylether, i.e. 0.09% in silicone.

The gel time is also found to be 13 seconds.

EXAMPLE 3

The same experiment as in example 1 is carried out while introducing the initiator P1 in a proportion of 9% in isopropanol, i.e. 0.08% in silicone.

The gel time, which is 3 minutes at ambient temperature, is recorded.

EXAMPLE 4

The same reaction as in example 1 is carried out but while introducing the initiator P1 in a proportion of 270 ppm in the polymer (S1) in the form of an 18% solution in butylether. The mixture is applied in a thin layer using a calibrated Meyer rod 0 so as to deposit 1.5 to 2 g/m² on a coated paper (Lohjan).

The shelf life in a stirred pot is 1 minute.

The coating polymerises in less than 30 s at 100° C. leading to a cross-linked coating exhibiting rub-off (gumming to touch).

The coating which has polymerised in one minute at 100° C. leads to a cross-linked layer exhibiting no rub-off and appears to be perfectly polymerised.

The polymerised layers obtained are then provided with an acrylic adhesive of the TESA4970® type. The complexes are subjected to a pressure of 70 g/cm² and the detachment forces are measured after 20 h at 70° C. by the FINAT No. 10 test and after 7 days at 70° C.

The detachment forces obtained by peeling at 180° C. on a dynamometer are lower than 20 g/cm.

EXAMPLE 5

The same reaction as in example 1 is carried out but while introducing the initiator P1 in a proportion of 900 ppm in the polymer (S1) in the form of a 9% solution in isopropanol. The mixture is applied in a thin layer using a calibrated Meyer rod 0 so as to deposit 1.5 to 2 g/m² on a Lohjan coated paper.

The shelf life in a stirred pot is 3 minutes.

The coating polymerises in less than 10 s at 100° C. leading to a cross-linked layer which has no rub-off and appears to be perfectly polymerised.

The polymerised layers obtained are then provided with an acrylic adhesive of the TESA4970 type for 15 minutes. The complexes are subjected to a pressure at 70 g/m² and the detachment forces are measured after 20 h at 70° C.

The detachment forces obtained by peeling at 180° of the adhesive on a dynamometer are lower than 50 cN/inch.

EXAMPLES 6 to 15

These examples show that the association of a trisarylborane with a cationic photoinitiator based on diaryliodonium or triarylsulfonium salt produces an increase in reactivity and lead to complete polymerisation.

The initiator P1 used is

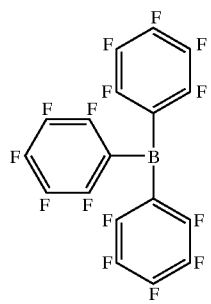

The photoinitiator PI used corresponds to the formula

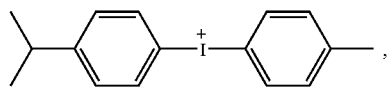

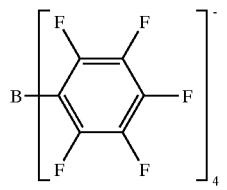

The silicone polymer used corresponds to the general formula

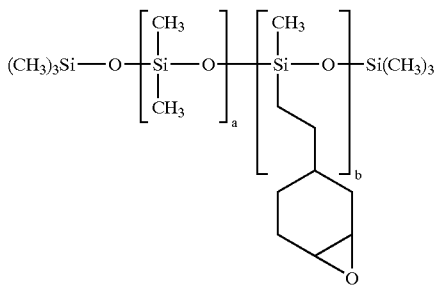

In the Case of Examples 6 to 10

The polymer (S1a) is used in a proportion of 950 g such that a=80; b=7

This polymer is stabilised by 50 ppm of HALS (TINUVIN 765)

A polymer (S1b) is also used in a proportion of 50 g such that a=220; b=3.8

The initiator P1 is added in a proportion of 0, 10, 25, 50 or 100 ppm to the two polymers S1a and S1b from five solutions of photoinitiator PI in a proportion of 18% in isopropanol with added initiator P1.

Ex. 6: Solution 1 containing 0% of P1 and 18% of PI: 25 g of solution 1 is added Ex. 7: Solution 2 containing 0.04% of P1 and 18% of PI: 25 g of solution 2 is added EX. 8: Solution 3 containing 0.1% of P1 and 18% of PI: 25 g of solution 3 is added Ex. 9: Solution 4 containing 0.2% of P1 and 18% of PI: 25 g of solution 4 is added Ex. 10: Solution 5 containing 0.4% of P1 and 18% of PT: 25 g of solution 5 is added The initiators in the silicone formulation are mixed using a Tripale mixer for half an hour at ambient temperature. The bath is stable for more than 24 hours.

The silicone is then applied to a polyester terephthalate film using coating rollers so that the coating is a layer of 1 g/m².

The speed of travel of the film is 100 m/min.

The film is exposed to a UV lamp having a power of 120 W/cm and an adhesive based on butyl acrylate in emulsion from the RHODOTAK range (RHODOTAK315P®) is applied immediately after exposure. The adhesive is dried at 110° C. in an oven either "in line" at the speed of travel of the film (100 m/min) or "off-line" independently on another line at a much faster speed of travel.

After the adhesive on the surface of the silicone coating has dried, the adhesive is transferred to a vellum paper using a transfer roller. A self-adhesive complex of which the detachment forces are measured during the period after compression of the labels under 70 g/cm² is thus obtained. The test is standardised and corresponds to the FINAT standards FINAT3=20 h at 20° C.

FINAT10=20 h at 70° C. which simulates natural ageing for 3 months at 20° C.

In the Case of Examples 11 to 15

The same coatings as in examples 6 to 10 are produced except that the silicone deposit is 1.5 g/m² in the case of a rougher substrate based on coated paper (Lopabase w67) produced by Lohjan.

The same measurements of detachment forces are taken in examples 11 to 15.

The results are expressed in cN/inch and presented in Table I.

TABLE I

| Example | PI (ppm) | P1 (ppm) | F3 cN/inch | F10 cN/inch |
| --- | --- | --- | --- | --- |
| 6 | 4300 | 0 | 5.08 | 61 |
| 7 | 4300 | 10 | 4.31 | 55.9 |
| 8 | 4300 | 25 | 4.57 | 50.8 |
| 9 | 4300 | 50 | 7.7 | 40.6 |
| 10 | 4300 | 100 | 5.08 | 30.5 |
| 11 | 4300 | 0 | 7.62 | 155 |
| 12 | 4300 | 10 | 4.57 | 88.9 |
| 13 | 43G0 | 25 | 7.62 | 96.5 |
| 14 | 4300 | 50 | 5.08 | 83.8 |
| 15 | 4300 | 100 | 0.35 | 55.9 |

Furthermore, the detachment forces evolve less with this type of adhesive which is reputed to be one of the most aggressive and is applied in an aqueous phase. Photocrosslinkable coatings are thus obtained cationically and rarely interact with the adhesives, in particular with acrylic adhesives. The detachment force decreases as the initiator 1 is added.

EXAMPLE 16

Example 10 is repeated while reducing the quantity of photointiator PI by two and keeping 100 ppm of trisarylborane in the final mixture.

Values equivalent to the test 6 without borane are found after measuring the detachment forces. The gain in photoinitiator is therefore multiplied by two.

TABLE II

| Example | F3 cN/inch | F10 cN/inch |
| --- | --- | --- |
| 16 | 5.08 | 55.9 |

What is claimed is:

1. A polymerizable and/or cross-linkable composition which comprises at least one polyorganosiloxane type monomer, oligomer and/or polymer with organofunctional groups, and an effective quantity of at least one heat-activated initiator comprising a boron derivative of formula (I)

$$(A)_xB(R')_y \qquad (I)$$

wherein the symbols R' are the same or different and represent
a linear or branched $C_1$–$C_{12}$ alkyl or alkenyl radical, optionally substituted by at least one electron-withdrawing group,
a linear or branched $C_1$–$C_{12}$ alkoxy radical, optionally substituted by at least one electron-withdrawing group,
a phenyl radical substituted by at least one electron-withdrawing group,
an aryl radical containing at least two aromatic rings, optionally substituted by at least one electron-withdrawing group,
a —$C_2H_4$—Si(Q)$_3$ radical with the symbols Q being the same or different and representing a $C_1$ to $C_{10}$ alkyl or alkoxy group or a siloxane oligomer with less than 10 silicone atoms, optionally substituted, by a radical of formula B(R')$_2$ with R' as defined above, or two R' groups may be bound to one another to form, with the boron atom to which they are bound, a cycle containing 5 or 10 atoms wherein said cycle is saturated, unsaturated, bridged or aromatic and optionally comprises one or more heteroatoms selected from the group consisting of oxygen, nitrogen and boron atoms, wherein the boron atom present in said cycle is optionally substituted by a radical as defined for A or R' in general formula I, the symbols A are independent of one another and represent:

a hydrogen atom, a halogen atom, or a hydroxyl radical, x represents 0 or the integer 1 or 2 and y represents an integer 1, 2 or 3 wherein the sum of x+y is equal to 3 and its solvated forms, and the group R' together with the group A contributes to a $\sigma_p$ at least equal to that of 3 (C$_6$H$_4$F) radicals.

2. The composition of claim 1, wherein at least one of the symbols R' represents a phenyl or aryl radical.

3. The composition of claim 1, wherein said initiator has the general formula (Ia)

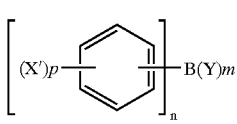
(Ia)

wherein n represents an integer between 1 and 3 and m an integer between 0 and 2 wherein the sum of n and m is equal to 3, the symbols Y are the same or different and represent a hydrogen atom, a hydroxyl group, a halogen atom, a linear or branched C$_1$–C$_{12}$ alkyl or alkenyl radical, substituted by at least one halogen atom element, a linear or branched C$_1$ to C$_{12}$ alkoxy radical, optionally substituted by at least one halogen atom element, a —C$_2$H$_4$—Si(Q)$_3$ wherein Q represents a C$_1$ to C$_{10}$ alkyl or alkoxy group or a siloxane oligomer with less than 10 silicone atoms, optionally substituted by a radical of formula B(R')$_2$ wherein R' is as defined above, or two groups Y optionally may be bound so as to form, with the boron atom to which they are bound, a C$_5$ to C$_{10}$ cycle wherein said cycle is saturated, unsaturated, bridged or aromatic and may comprise one or more heteroatoms selected from the group consisting of oxygen, nitrogen and boron atoms, wherein the boron atom present in said cycle optionally is substituted by a radical as defined for Y in general formula (Ia) and the symbols X' are the same or different and represent a halogen atom, a linear, branched, mono- or polycyclic, saturated, unsaturated or aromatic C$_1$ to C$_{12}$ hydrocarbon radical optionally substituted by at least one halogen atom element or a linear or branched, mono-, poly or perhalogenated C$_1$ to C$_{12}$ alkyl radical, and the indices p are the same or different and represent an integer between 0 and 5.

4. The composition of claim 1, wherein said initiator is selected from the following compounds:

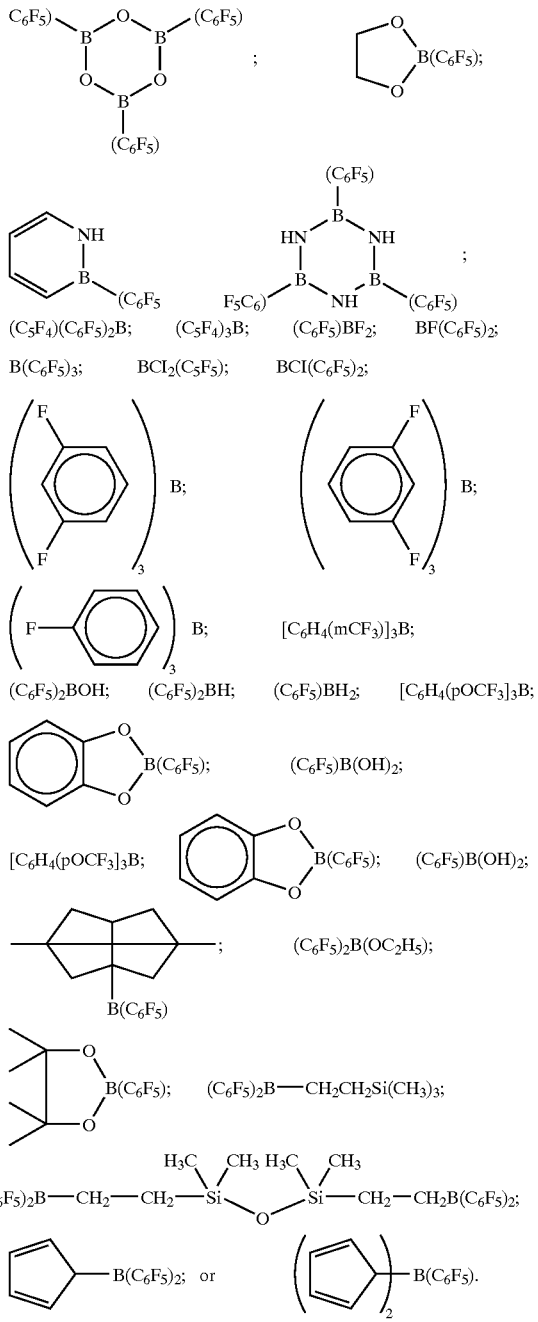

5. The composition of claim 1, wherein said initiator is used in solution in a solvent.

6. The composition of claim 1, wherein the initiator is used in a proportion of 0.0001 to 5 parts by weight per 100 parts by weight of the dry substance in polyorganosiloxane type monomers, oligomers and/or polymers with organofunctional groups.

7. The composition of claim 1, wherein the polyorganosiloxane type monomers, oligomers and/or polymers contain epoxide, oxetane, dioxolane and/or alkenylether groups as organofunctional groups.

8. The composition of claim 1, wherein the type polyorganosiloxane monomers, oligomers and/or polymers with organofunctional groups comprise units of formula (II) and are terminated by units of formula (III) or cyclic groups comprising units of formula (II) shown below:

wherein the symbols $R^1$ and $R^2$ are similar or different and represent:

a linear or branched alkyl radical containing 1 to 8 carbon atoms, optionally substituted by at least one halogen, a cycloalkyl radical containing between 5 and 8 cyclic carbon atoms, optionally substituted, an aryl radical containing between 6 and 12 carbon atoms optionally substituted, an aralkyl radical having an alkyl portion containing between 5 and 14 carbon atoms and an aryl portion containing between 6 and 12 carbon atoms, optionally substituted on the aryl portion by halogens, alkyls and/or alkoxyls containing 1 to 3 carbon atoms, the symbols Z are similar or different and represent:

an $R^1$ and/or $R^2$ group, a hydrogen radical, and/or a cross-linkable organofunctional group bound to the silicone of the polyorganosiloxane via a divalent radical containing 2 to 20 carbon atoms and optionally containing at least one heteroatom, wherein at least one of the symbols Z represents a cross-linkable functional organic group.

9. The composition of claim 1, wherein the organofunctional groups are selected from the group consisting of:

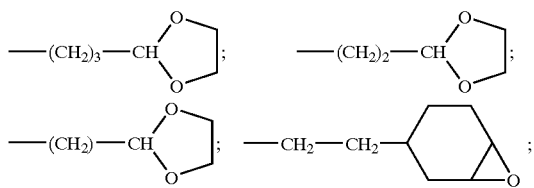

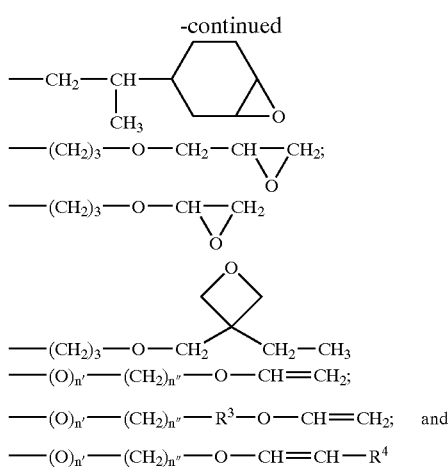

wherein n' represents 0 or 1 and n" represents an integer between 1 and 5

$R^3$ represents a linear, branched or cyclic $C_1$ to $C_{12}$, optionally substituted, alkylene radical or an optionally substituted $C_5$ to $C_{12}$ arylene radical, and $R^4$ represents a linear or branched $C_1$ to $C_6$ alkyl radical.

10. The composition of claim 1, wherein at least one of the symbols R' represents a phenyl, tolyl or dichlorophenyl radical.

11. The composition of claim 1, wherein it further comprises a cationic photoinitiator.

12. Resin comprising the composition of claim 1.

13. Polymer comprising the composition of claim 1.

14. Coating comprising the resin according to claim 12.

15. Coating according to claim 14, wherein said coating is a varnish, an adhesive coating, an anti-adhesive coating and/or an ink.

16. Dental composition comprising the composition of claim 1.

17. Dental composition according to claim 16, wherein it is a dental prosthesis or a dental restoration material.

18. Object having at least one surface coated with a resin according to claim 12.

19. A method for polymerising and/or cross-linking a composition according to claim 1 comprising the following steps of:

(1) exposing the composition to a source of heat, and (2) polymerising and/or cross-linking the composition.

* * * * *